(12) United States Patent
Joshi et al.

(10) Patent No.: US 11,769,479 B2
(45) Date of Patent: Sep. 26, 2023

(54) SYSTEM AND METHOD FOR PRODUCING SOUND SIGNALS

(71) Applicants: Suneet Joshi, Chandigarh-UT (IN); Mahipal Chaudhri, Rochester, NY (US); Yashwant Chaudhri, San Diego, CA (US)

(72) Inventors: Suneet Joshi, Chandigarh-UT (IN); Mahipal Chaudhri, Rochester, NY (US); Yashwant Chaudhri, San Diego, CA (US)

(73) Assignee: Yashwant Chaudhri, San Diego, CA (US)

( * ) Notice: Subject to any disclaimer, the term of this patent is extended or adjusted under 35 U.S.C. 154(b) by 208 days.

(21) Appl. No.: 17/343,514

(22) Filed: Jun. 9, 2021

(65) Prior Publication Data
US 2021/0398516 A1    Dec. 23, 2021

(51) Int. Cl.
| | |
|---|---|
| *G10K 15/02* | (2006.01) |
| *G10L 25/06* | (2013.01) |
| *G10L 25/18* | (2013.01) |
| *G06T 7/90* | (2017.01) |
| *A61B 5/00* | (2006.01) |
| *G10L 25/51* | (2013.01) |

(52) U.S. Cl.
CPC ............ *G10K 15/02* (2013.01); *A61B 5/0077* (2013.01); *A61B 5/4854* (2013.01); *A61B 5/742* (2013.01); *G06T 7/90* (2017.01); *G10L 25/06* (2013.01); *G10L 25/18* (2013.01); *G10L 25/51* (2013.01); *G06T 2207/10024* (2013.01); *G06T 2207/30196* (2013.01)

(58) Field of Classification Search
CPC .................................................... G10K 15/02
See application file for complete search history.

(56) References Cited

U.S. PATENT DOCUMENTS

| | | | |
|---|---|---|---|
| 7,537,576 | B1 | 5/2009 | Worley, III |
| 8,860,748 | B2 | 10/2014 | Campbell et al. |
| 2006/0199715 | A1 | 9/2006 | Leon |
| 2017/0119994 | A1* | 5/2017 | Argaman ............. A61B 5/0205 |
| 2019/0298966 | A1* | 10/2019 | Mawson ............... A61M 21/02 |
| 2021/0308413 | A1* | 10/2021 | Pierne .................. G10H 1/0008 |

OTHER PUBLICATIONS

First Examination Report received for Indian Patent Application No. 202011025217, dated Nov. 21, 2022, 6 pages.

* cited by examiner

*Primary Examiner* — Olisa Anwah
(74) *Attorney, Agent, or Firm* — Shook, Hardy & Bacon L.L.P.

(57) ABSTRACT

A system and method for producing sound signals that comprises an image capturing device to capture an auric color representation of a body part of a person. The auric color representation represents a blocked energy area of the body part. A processing device divides the auric color representation into a plurality of arcs. A display device communicating with the processing device displays the plurality of arcs. A transcranial sound stimulation device determines a block-breaking frequency corresponding to the blocked energy area. A tone generator generates a set of wave-patterns corresponding to the block-breaking frequency. An audio device produces sound signals based on the set of wave-patterns, to be heard by the person thereby healing the blocked energy area of the body part.

20 Claims, 6 Drawing Sheets

SYSTEM AND METHOD FOR PRODUCING SOUND SIGNALS

FIELD OF THE INVENTION

The invention relates to a system and method for producing sound signals. More particularly, it relates to a system and a method for producing sound signals corresponding to at least one blocked energy area of at least one body part of a person.

CROSS REFERENCE TO RELATED INVENTION

This invention takes priority from an earlier filed Indian patent application no. 202011025217 filed on Jun. 16, 2020; which is incorporated herein by reference in its entirety.

BACKGROUND OF THE INVENTION

The ancient philosophies of various civilizations like India, Greece, Egypt, China, and Rome presents living beings as outflowing a vital energy field. The energy field outflow is also mentioned as, "a spiritual sphere surrounding everyone, as well as a natural and corporal one," and is well known in the art.

The universal life force resides in living beings at different energy centers called chakras or a spiritual sphere, a Sanskrit term meaning "wheels." Chakras are shaped in the form of a lotus with different colored petals. Each chakra radiates a specific color based on energy residing in it. A human body comprises of seven major chakras and a plurality of minor ones. The chakras lie along spinal column, starting from the base of the spine, forming first chakra, to the top of the head, forming seventh chakra. As per scriptures already known in the art, Spine comprises subtle Sushumana path way, that further includes Vajra having Chitrani like coaxial tubes. The central axis is known as Brahm Nadi. The chakras are located on the Brahm Nadi. Different chakras have different number of petals attributed to them.

Mooladhar Chakra ($1^{st}$ Chakra at the base around Anus) has four petals; Swadhishthan Chakra ($2^{nd}$ Chakra in Euro Genital area) has six petals; Manipur Chakra ($3^{rd}$ Chakra in Digestive stomach area) has 10 petals; Anahat Chakra ($4^{th}$ Chakra in the chest area) with 12 petals; Vishudhi Chakra ($5^{th}$ Chakra in the throat) with 16 petals; Ajna Chakra ($6^{th}$ Chakra at Pineal gland, at the level of eye brow center) with 2 petals and Sahasrar Chakra ($7^{th}$ Chakra) having $20 \times 50 = 1000$ petals at the crown of the head.

The seven major chakras are directly concerned with physical health of the human body. Before arising of any disease in the physical body it is first exhibited at the brain level in form of blocked energy at a specific location. If the blockage persists for more than three months, physical disease or symptoms in the body starts appearing. Energy blockage or sluggishness in a chakra leads to disturbance in the body, thus affecting health of a person, therefore, maintaining optimal energy levels of the chakras is of vital importance for mental, emotional, and physical well-being of the body.

SUMMARY OF THE INVENTION

It is an object of the invention to provide a system and a method for producing sound signals corresponding to an at least one blocked energy area of at least one body part of a person.

It is an object of the invention to provide a system for producing sound signals, wherein the system comprising: an image capturing device to capture an auric color representation of at least one body part of a person, wherein the auric color representation represents at least one blocked energy area of the at least one body part; at least one processing device configured to divide the auric color representation into a plurality of arcs; a display device to display the plurality of arcs processed by the at least one processing device; a transcranial sound stimulation device to determine at least one block-breaking frequency corresponding to the at least one blocked energy are the person; a tone generator to generate a set of wave-patterns corresponding to the at least one block-breaking frequency; and an audio device to produce sound signals based on the set of wave-patterns.

It is another object of the invention to provide a system for producing sound signals, wherein the auric color representation represents energy areas of the at least one body part.

It is another object of the invention to provide a system for producing sound signals, wherein the energy areas comprise at least one of blocked energy areas, unblocked energy areas, and a combination thereof.

It is another object of the invention to provide a system for producing sound signals, wherein the plurality of arcs divided by the processor represents a plurality of images of the at least one body part.

It is another object of the invention to provide a system for producing sound signals, wherein the transcranial sound stimulation comprises a frequency determination module configured to determine the at least one block-breaking frequency corresponding to the at least one blocked energy area based on correlation of the set of sub-frequencies with the plurality of arcs.

It is another object of the invention to provide a system for producing sound signals, wherein the frequency determination module is configured to: determine a first frequency based on a speech sample of the person; determine a second frequency corresponding to the at least one body part based on the first frequency and divide the second frequency into a set of sub-frequencies, and determine the at least one block-breaking frequency corresponding to the at least one blocked energy area based on correlation of the set of sub-frequencies with the plurality of arcs.

It is another object of the invention to provide a system for producing sound signals, wherein the set of wave-patterns comprises at least one of sawtooth wave, triangular wave, square wave, sine wave, or a combination thereof.

It is another object of the invention to provide a system for producing sound signals, wherein the sound signals can be heard by the person to heal the at least one blocked energy area of the at least one body part.

It is another object of the invention to provide a system for producing sound signals, wherein the sound signals are to be heard by the person at recurrent intervals in a time frame to monitor condition of the person.

It is another object of the invention to provide a method for producing sound signals, wherein the method comprising: capturing an auric color representation of at least one body part of a person by an image capturing device, wherein the auric color representation represents at least one blocked energy area of the at least one body part; dividing the auric color representation into a plurality of arcs by a processing device; displaying the plurality of arcs by a display device; determining at least one block-breaking frequency corresponding to the at least one blocked energy area by a transcranial sound stimulation device; generating a set of wave-patterns corresponding to the at least one block-breaking frequency by a tone generator; and producing sound signals based on the set of wave-patterns by an audio device.

It is another object of the invention to provide a method for producing sound signals, wherein the auric color representation represents energy areas of the at least one body part.

It is another object of the invention to provide a method for producing sound signals, wherein the energy areas comprise at least one of blocked energy areas, unblocked energy areas, and a combination thereof.

It is another object of the invention to provide a method for producing sound signals, wherein the plurality of arcs divided by the processor represents a plurality of images of the at least one body part.

It is another object of the invention to provide a method for producing sound signals, wherein the transcranial sound stimulation comprises a frequency determination module configured to determine the at least one block-breaking frequency corresponding to the at least one blocked energy area based on correlation of the set of sub-frequencies with the plurality of arcs.

It is another object of the invention to provide a method for producing sound signals, wherein the frequency determination module is configured to: determine a first frequency based on a speech sample of the person; determine a second frequency corresponding to the at least one body part based on the first frequency and divide the second frequency into a set of sub-frequencies, and determine the at least one block-breaking frequency corresponding to the at least one blocked energy area based on correlation of the set of sub-frequencies with the plurality of arcs.

It is another object of the invention to provide a method for producing sound signals, wherein the set of wave-patterns comprises at least one of sawtooth wave, triangular wave, square wave, sine wave, or a combination thereof.

It is another object of the invention to provide a method for producing sound signals, wherein the sound signals can be heard by the person to heal the at least one blocked energy area of the at least one body part.

It is another object of the invention to provide a method for producing sound signals, wherein the sound signals are to be heard by the person at recurrent intervals in a time frame to monitor condition of the person.

The present invention provides systems and methods for producing sound signals to heal blocked energy areas in one or more body parts of a person. The one or more body parts are, but not limited to, brain, respiratory system, digestive system, circulatory system, excretory system, nervous system, etc. Further, each body part is associated with a particular frequency. The system comprises generating sound signals of the particular frequency, which when heard by the person, leads to healing of the blocked energy areas by breaking the blocks and ensuring smooth flow of energy at the specific point or location.

Aura photography is used as a diagnostic tool to assess percentage of energy blocks in the brain due to stress, anxiety, and depression. An auric color representation represents one or more energy areas in a body part. The auric color representation comprises different colors corresponding to different amount of energies in the body part. The colors change according to state of the body part.

Blocked energy areas are represented by dark maroon color. Upon achieving greater free flow of energy in the blocked energy areas, the dark maroon color may change to green, blue etc. Different colors in the auric color representation are associated with different energy levels of the body part. The auric color representation is divided into a plurality of arcs to be displayed. Further, one or more block-breaking frequencies corresponding to the blocked energy areas are determined based on speech of the person. The block-breaking frequencies when heard by the person, leads to breakage of the blocked energy areas, thereby healing the person. The block-breaking frequency is unique for everyone and each blocked energy area in the body part.

According to an embodiment of the invention, a speech frequency of the person is associated with a fifth energy center or chakra. The speech frequency corresponds to throat signals, where the throat area forms the fifth energy center or fifth chakra or Vishudhi Chakra among seven chakras. The systems and methods of the invention utilize an octave chart to determine a block-breaking frequency. The block-breaking frequency corresponds to frequency of the blocked energy area of the body part. Further, a set of wave-patterns are generated based on the block-breaking frequency, where the set of wave-patterns are used to produce sound signals to be heard by the person thereby healing the blocked energy area of the body part.

Brain frequency is given in four wave forms such as Square, Sawtooth, Triangle and Sine waves. Location and duration of treatment is calculated and adjusted as per clinical symptoms of person. Commonly used electronic devices such as phone, lap-top and/or desktop are used for the sound delivery using ears between 45-85 percent volume, depending upon frequency heard, for about 25-30 minutes per treatment, once or twice a day for a total of 3-9 weeks.

In another embodiment of the invention, the sound signals are heard by the person at recurrent intervals in a time frame to monitor condition of the person. The sound signals are heard by the person for a period of 30 minutes. At the end of the period, the auric color representation of the body part is captured to determine energy levels of the body part, and accordingly, the sound signals are again heard by the person for a period of 30 minutes. This process is repeated until the auric color representation of the body part of the person shows healed energy areas.

BRIEF DESCRIPTION OF THE DRAWINGS

Embodiments of the invention are best understood by reference to the figures and description set forth herein. All the aspects of the embodiments described herein will be better appreciated and understood when considered in conjunction with the following description and the accompanying drawings.

DETAILED DESCRIPTION OF THE INVENTION

Figure 1:
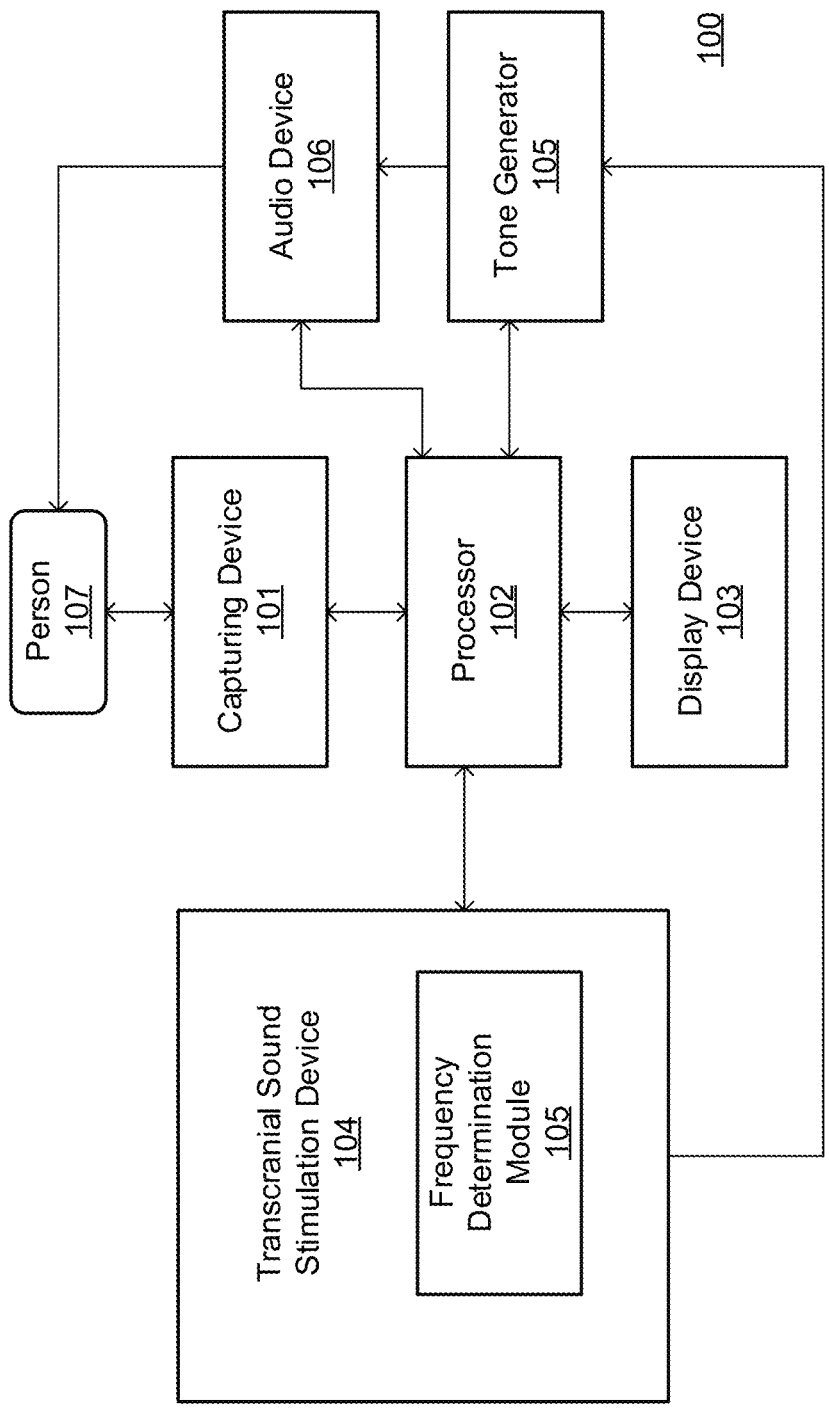
FIG. 1 shows a system for producing sound signals according to an embodiment of the invention.

Embodiments of the present invention are best understood by reference to the figures and description set forth herein.

All the aspects of the embodiments described herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit and scope thereof, and the embodiments herein include all such modifications.

Chakras play an important role in well-being of a human body. Stress, anxiety, insomnia and various such functional factors lead to imbalance in energies of the chakras, thus resulting in energy blockages in the chakras located at various body parts. The energy blockages in the chakras results in mental and physical disorders, anxiety, fear, instability, emotional imbalance, low energy, fatigue, scarcity of creativity, dearth of imagination, etc.

There are various existing arts to heal energy blockages in the chakras. Few of such methods are magnetic resonance imaging of brain, physical fitness regimen with color healing, combination of several scientific disciplines to treat energy blockages in chakras such as yoga, massage, metaphysics, prayer, traditional western medicine or vibrational energy therapy.

One of such methods is sound based healing to heal the energy blockages at various body parts. The body parts may include, but not limited to, brain, respiratory system, digestive system, circulatory system, excretory system, nervous system, etc. Further, each body part is associated with a particular frequency. The sound based healing involves generating sound signals of the particular frequency, which are passed through auditory nerve to the mid brain and are heard by the person, in order to break the energy blockages. By using sound based healing, affected body part is healed inside out. Unlike many other systems, in which electromagnetic waves are provided to the person, that travel from outside the skull and penetrates 1.5-2 cm into the brain. The invention utilizes sound waves that are provided to middle of the brain and travel outwards towards surface of the brain in order to deal with aspects of problem.

There are several existing prior arts disclosing an aura of the human body. The aura is energy field surrounding the human body. The energy field is magnetic energy field that represents information about events inside the human body and is thus linked to internal health. Blockage of the energy field leads to health issues. The invention is directed towards a system and a method for producing sound signals corresponding to an at least one blocked energy area of at least one body part of a person. Thereon, a sound-based healing of a person to heal blocked energy areas in at least one body part of the person.

The invention involves capturing and displaying an auric color representation of the body part of the person. The auric color representation represents one or more blocked or unblocked or combination of both blocked and unblocked energy areas in the body part. One or more block-breaking frequencies corresponding to blocked energy areas in one or more body parts are determined. A tone generator generates a set of wave-patterns corresponding to the block-breaking frequency. An audio device produces sound signals, based on the set of wave-patterns, to be heard by the person thereby healing the blocked energy area of the body part.

Referring to the figures, wherein the components are labeled with like numerals throughout the several figures, and initially referring to FIG. 1, illustrates a block diagram of an illustrated embodiment of a system 100 for producing sound signals for a person 107, wherein the sound signals can be heard by the person to heal blocked energy areas in a body part of the person 107. The system 100 comprises a Transcranial Sound Stimulation Device 104, Frequency Determination Module 105, Person 107, Capturing Device 101, Processor 102, Display Device 103, Audio Device 106, and Tone Generator 105. In an embodiment of the invention, the components and arrangement of the components included in the system 100 may vary. In another embodiment of the invention, the system 100 may further comprise other components that perform or assist in the performance of one or more processes.

The body part may include, but not limited to, brain, respiratory system, digestive system, circulatory system, excretory system, nervous system, etc.

FIG. 1 shows the system 100 for producing sound signals. An image capturing device 101 captures an auric color representation of the body part of a person 107. The image capturing device 101 may be, but not limited to, an aura scanner, a digital camera, etc. The auric color representation represents one or more energy areas in the body part. The energy areas comprise blocked energy areas, unblocked energy areas, or a combination of blocked energy areas and unblocked energy areas.

The auric color representation comprises different colors corresponding to different amount of energies in the body part. The colors in the auric color representation change according to state of the body part. Energies of the body part are associated to colors, chakras and musical tones as they all resonate to same frequency. In other words, sound, light and color are interconnected at source. Thus, different colors in the auric color representation demonstrate different energy levels of the captured body part.

The processor 102, as shown in the FIG. 1, divides the auric color representation into a plurality of arcs, starting from the left anterior portion of the shoulder line in a clock-wise direction and ending at the left posterior point. The processor 102 may be, but not limited to, a microprocessor, a microcontroller, a graphical processor, a GPU, graphic cards, a GPGPU, etc. The plurality of arcs represents a plurality of images of the body part. Number of arcs may depend upon various parameters, such as, the body part to be healed/treated, amount of energy blockage in the body part, to what extent the energy blockage is to be treated, etc. In an embodiment of the invention, the plurality of arcs is fifty, where each arc corresponds to 7.2 degrees. A display device 103 receives the plurality of arcs from the processor 102 and displays the plurality of arcs of the body part. The display device 103 is, but not limited to, a screen, a projector, a multi-media device, a monitor, TV screen, LCD screen, an electronic device, a plasma screen, etc.

According to another embodiment of the invention, the processor 102 may be an application-specific integrated computer (ASIC), a general-purpose computer, a central processing unit (CPU) or other programmable devices for general purpose or special purpose such as a microprocessor and a digital signal processor (DSP), a programmable controller, a programmable logic device (PLD) or a combination thereof. In another embodiment of the invention, the processor 102 may be configured as an apparatus, a system, or the like based on the implementation of instructions that perform one or more operations as disclosed herein. In another embodiment of the invention, the processor 102 may be a standalone, or may be a part of subsystem of a larger system.

In addition, a transcranial sound stimulation device 104, as shown in FIG. 1, determines one or more block-breaking frequencies corresponding to blocked energy areas in one or more body parts. A block-breaking frequency represents a particular frequency associated with a particular blocked energy area in a body part. The block-breaking frequency when heard by the person 107, leads to breakage of the energy area blockage, thus healing the person 107. The block-breaking frequency is unique for each individual and each blocked energy area.

The transcranial sound stimulation device 104 comprises a frequency determination module 105 to determine the block-breaking frequency corresponding to the blocked energy area in the body part. The frequency determination module 105 determines a first frequency based on a speech sample of the person 107, a second frequency corresponding to the body part based on the first frequency and a set of sub-frequencies on the basis of the second frequency. The transcranial sound stimulation device 104 further determines the block-breaking frequency based on the set of sub-frequencies.

The speech sample of the person 107 may be taken by using, but not limited to, a microphone, a voice recorder, a multimedia device, etc. A voice analyzer (not shown here) analyzes the speech sample of the person 107 to determine a speech frequency. The speech frequency is as unique to every human body, as is the fingerprint. The speech frequency is associated with a fifth energy center or chakra. In other words, the speech frequency corresponds to throat signals, where the throat area forms the fifth energy center or fifth chakra among the seven chakras or Vishudhi Chakra (with sixteen petals representing 16 vowels of Hindi script).

The frequency determination module 105 uses an octave chart as shown in Table 1 to calculate the first frequency, the second frequency, the set of sub-frequencies and the block-breaking frequency. In general, the speech frequency of the person 107 lies between second and third octaves in the octave chart. Therefore, the frequency determination module 105 uses first, second, third and fourth octaves in the octave chart to calculate the first frequency, the second frequency, the set of sub-frequencies and the block-breaking frequency. The frequency determination module 105 compares the speech frequency of the person 107 to a nearest value in the octave chart in order to determine the first frequency. The first frequency thus obtained is associated with the fifth energy center or fifth chakra or Vishudhi Chakra among the seven chakras.

Further, the frequency determination module 105 determines exact location of the first frequency in the octave chart to calculate frequency values of all other six energy centers or chakras from the octave chart. Four values down and two values up the first frequency in the octave chart leads to determination of the frequency values of the six energy centers or chakras. Frequency value of the energy center associated with the body part having blocked energy areas to be treated is the second frequency value. Thus, the second frequency value corresponds to the body part to be treated.

The frequency determination module 105 divides the second frequency value into the set of sub-frequencies on the basis of a mathematical formula computed by the processor 102. The set of sub-frequencies may range from two to fifty. The set of sub-frequencies is associated with the energy center or chakra of the body part of the person 107. Different body parts lead to different set of sub-frequencies. Moreover, the set of sub-frequencies is associated with the plurality of arcs. As many as arcs in the plurality of arcs, as many as sub-frequencies in the set of sub-frequencies are generated. Thus, there is one-to-one correlation between the plurality of arcs and the set of sub-frequencies. In an embodiment of the invention, the set of sub-frequencies is fifty.

The block-breaking frequency is determined based on the correlation of the set of sub-frequencies with the plurality of arcs. The block-breaking frequency corresponds to frequency of the blocked energy area of the body part. In an embodiment of the invention, the fifty sub-frequencies are correlated with the fifty arcs to determine a block-breaking frequency among the fifty sub-frequencies for an arc representing energy blockage. Each arc of the plurality of arcs is associated with each block-breaking frequency in the set of sub-frequencies.

TABLE 1

| Octave | Zero | $1^{st}$ | $2^{nd}$ | $3^{rd}$ | $4^{th}$ | $5^{th}$ | $6^{th}$ | $7^{th}$ | $8^{th}$ | $9^{th}$ | $10^{th}$ |
|---|---|---|---|---|---|---|---|---|---|---|---|
| Hertz → | | | | | Standard Frequency Chart as Per Indian Sargam | | | | | | |
| Note ↓ | | | | | | | | | | | |
| Sa (C) | 16.35 | 32.7 | 65.4 | 130.81 | 261.63 | 523.25 | 1046.5 | 209.3 | 4186 | 8372 | 16744 |
| Re (D) | 18.354 | 36.706 | 73.416 | 146.83 | 233.66 | 587.33 | 1174.4 | 2343.3 | 4698.6 | 9397.3 | 18794 |
| Ga (E) | 20.602 | 41.203 | 62.407 | 164.83 | 329.63 | 659.26 | 1318.5 | 263.7 | 5174 | 10548 | 21096 |
| Ma (F) | 21.827 | 43.654 | 87.307 | 174.63 | 349.23 | 698.46 | 1396.6 | 2793.8 | 5587.7 | 11175 | 22350 |
| Pa (G) | 24.5 | 48.999 | 97.999 | 195 | 392 | 783.99 | 1586.5 | 3136 | 6271.9 | 12543 | 25087 |
| Dha (A) | 27.5 | 55 | 110 | 22 | 440 | 880 | 1760 | 3520 | 7040 | 14580 | 28180 |
| Ni (B) | 30.68 | 61.736 | 123.47 | 246.94 | 493.88 | 987.77 | 1975 | 3951.1 | 7902.1 | 15804 | 31606 |

A tone generator 105 according to FIG. 1 generates a set of wave-patterns corresponding to the block-breaking frequency. The set of wave-patterns comprises, but not limited to, sawtooth waveform, triangular waveform, square waveform, sine waveform, etc. The sawtooth waveform has zero rake angle, ramps upwards and drops sharply and reverse sawtooth waveform ramps downwards and rises sharply. The triangular wave form has a gradual rise and a gradual fall. In the square wave, amplitude alternates between fixed minimum and maximum with same duration. Transition from minimum to maximum or vice versa is instantaneous. The square waveform has equal high and equal low. The sine waveform is a continuous wave with smoothest periodic function or oscillation as compared to other waveforms.

An audio device 106, according to FIG. 1, produces sound signals, based on the set of wave-patterns, to be heard by the person 107 thereby healing the blocked energy area of the body part. The sound signals have a frequency range from 20 Hz to 20 MHz and are audible by the person 107. The sound signals are heard by the person 107 at recurrent intervals in a time frame to monitor condition of the person 107. According to an embodiment of the invention, the sound signals are heard by the person 107 for the period as recommended by a psychiatrist.

Further, the psychiatrist may be, but not limited to, a medical practitioner, a health practitioner, a psychologist, a counsellor, a therapist, a psychoanalyst, a psychotherapist, a shrink, a doctor, a healer, an alienist, an analyst etc.

According to another embodiment of the invention, the sound signals are heard by the person 107 for a period of, but not limited to, 3 minutes-40 minutes. At the end of the time period, the capturing device 101, as shown in FIG. 1, captures the auric color representation of the body part of the person 107 in order to determine blocked energy areas of the body part of the person 107, and the sound signals are again heard by the person 107 for a time period of, but not limited to, 3 minutes-40 minutes, on the basis of the auric color representation of the body part of the person 107. This process is repeated until the auric color representation of the body part of the person 107 shows healed energy areas.

According to another embodiment of the invention, different wave-patterns in the set of wave-patterns are randomly heard by the person 107 for a period of, but not limited to, 3 minutes-40 minutes. Thus, the set of wave-patterns may comprise any waveform for any time duration.

According to another embodiment of the invention, different wave-patterns in the set of wave-patterns are heard by the person 107 for a period of, but not limited to, 3 minutes-40 minutes. in a particular sequence. For instance, the sawtooth waveform is heard for first 8 minutes followed by the triangular waveform for 8 minutes, then the square waveform for next 5 minutes and the sine waveform for last 9 minutes. The square waveform and the sawtooth triangular waveform are believed to break the energy blockage in the body part of the person 107, whereas the triangular waveform and the sine waveform are believed to smooth the energy blockage in the body part of the person 107. Further, the sequence of the waveforms may be changed by a psychiatrist.

Further, the psychiatrist may be, but not limited to, a medical practitioner, a health practitioner, a psychologist, a counsellor, a therapist, a psychoanalyst, a psychotherapist, a shrink, a doctor, a healer. an alienist, an analyst, etc.

Figure 2:
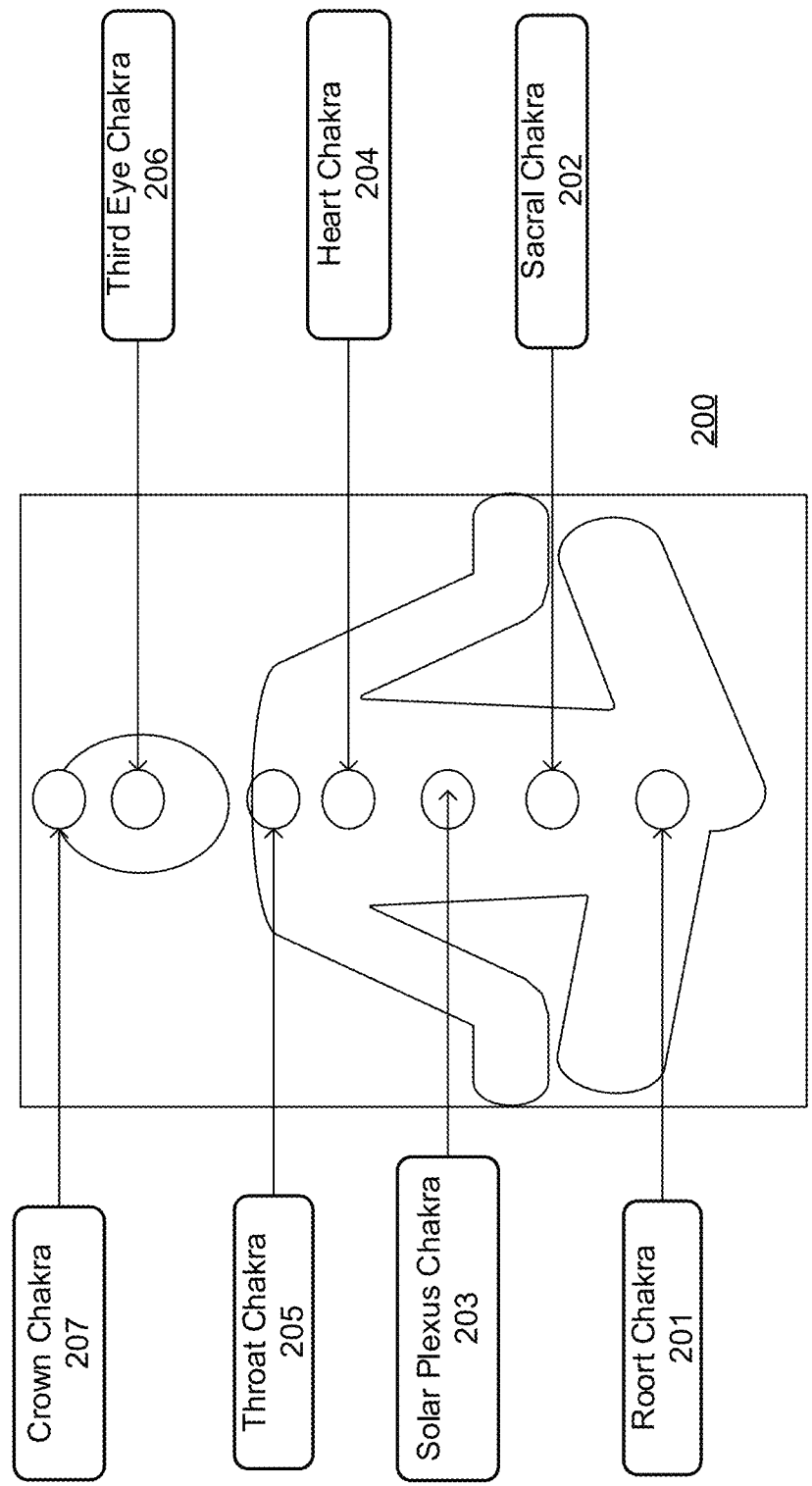
FIG. 2 shows a representation of chakras in a human body.

FIG. 2 shows a representation 200 of chakras of a human body. The body comprises various major and minor chakras. There are seven major chakras (201-207) and a plurality of minor chakras, not shown here. According to the representation 200, the seven major chakras (201-207) run along spinal column of the body. The chakras represent a plurality of energy centers in the body. The energy centers are also known as energy areas, energy blocks, energy sphere etc.

The seven chakras (201-207) represent seven energy blocks in the body. The chakras (201-207) lie along the spinal column, starting at base of the spinal column to top of the spinal column. Each chakra in the seven chakras (201-207) vibrates at a certain frequency, wherein the first chakra 201 vibrating slowest and the seventh chakra 207 vibrating fastest. Further, each chakra in the seven chakras (201-207) has a specific meaning and color.

At base of the spinal column, a first chakra 201, known as root chakra is formed. The second chakra, Sacral chakra 202 is formed above the first chakra 201; the third chakra is Solar Plexus chakra 203 above the Sacral Chakra 202; the fourth chakra is Heart Chakra 204; the fifth chakra is Throat Chakra 205; the sixth chakra is Third Eye chakra 206 and the seventh chakra is Crown chakra 207 formed at the top of the head.

If energy level of a chakra among the seven chakras (201-207) gets disrupted or blocked, it leads to various mental or health disorders. Thus, it is highly important to maintain the energy level of the chakras. Moreover, balancing of the seven chakras (201-202) is equally important. If the balancing of the chakras is disrupted or damaged, it may lead to serious problems relating to physical, emotional and psychological well-being of the body.

Figure 3:
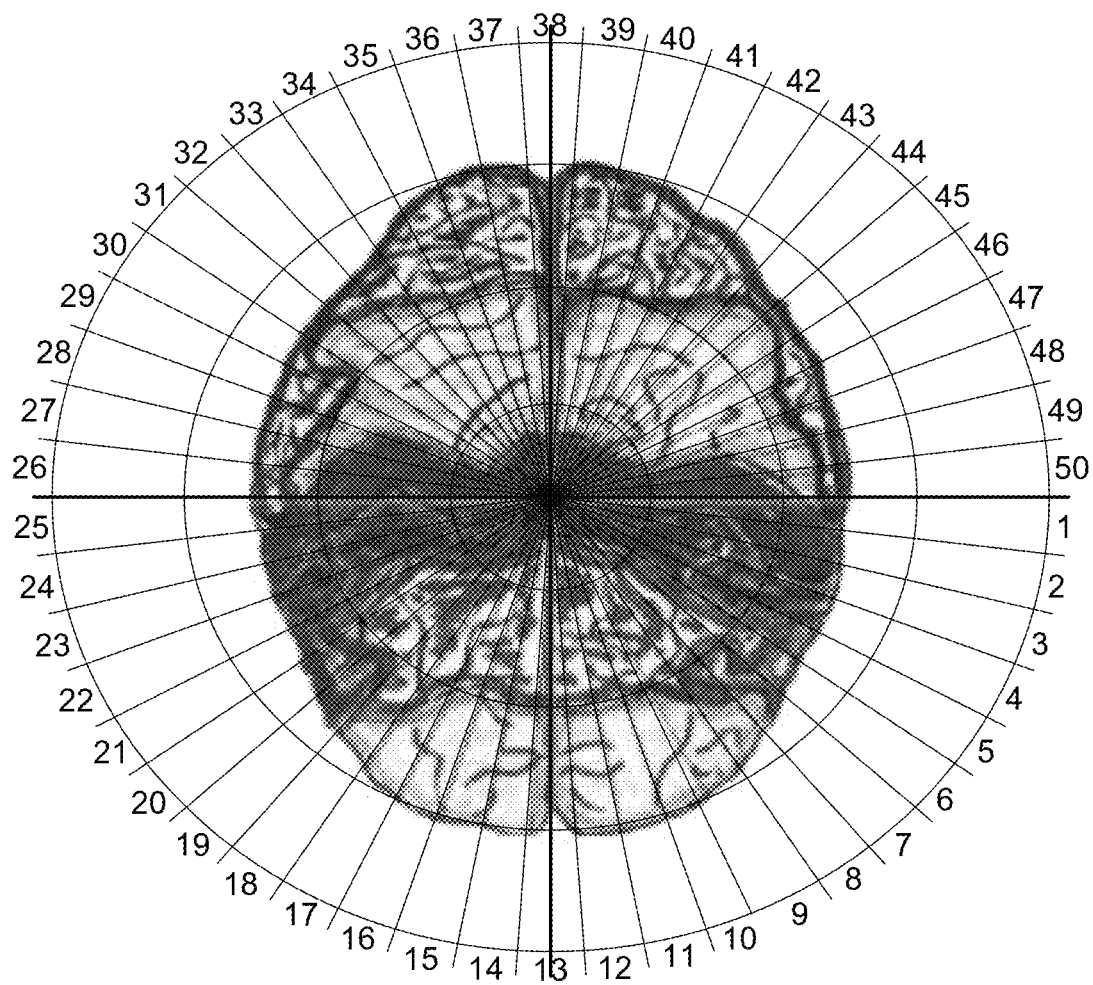
FIG. 3 shows an auric color representation of brain of a person.

FIG. 3 shows an auric color representation 300 of brain of a person. An image capturing device 101, as previously shown in FIG. 1, captures the auric color representation 300 of the brain. The image capturing device 101 includes, but not limited to, an aura scanner, a digital camera, etc. The auric color representation 300 represents one or more energy areas in the brain. The energy areas comprise blocked energy areas, unblocked energy areas, or a combinations of blocked energy areas and unblocked energy areas. Moreover, the auric color representation 300 comprises different colors corresponding to different amount of energies in different parts of the brain. The colors in the auric color representation 300 change according to state of the brain.

Further, according to this embodiment of the invention, colors shown in the auric color representation 300 are for distinguishing different areas of the brain but are not limiting the scope of the invention. The colors are not representing actual auric color but are for illustration purpose only.

A processor 102, as previously shown in the FIG. 1, divides the auric color representation 300 into fifty arcs. The processor 102 may be, but not limited to, a microprocessor, a microcontroller, a graphical processor, a GPU, graphic cards, a GPGPU, etc. The fifty arcs represent energy levels of different parts of the brain. Number of arcs may depend upon various parameters, such as, amount of energy blockage in the brain, to what extent the energy blockage is to be treated, etc. Each arc of the fifty arcs corresponds to 7.2 degrees. Blocked energy areas in the brain are located based on fifty arcs, where the fifty arcs are formed by starting from left shoulder side of the person and moving in a clockwise direction to right shoulder side of the person. Therefore, the fifty arcs are formed by starting from frontal left quadrant to frontal right quadrant to rear right quadrant and lastly to rear left quadrant of the brain to locate exact spot of the energy blockage in form of arc number in the brain.

A display device 103, as previously shown in FIG. 1, receives the fifty arcs from the processor 102 and displays the arcs of the brain in a colored pattern. The display device 103 is, but not limited to, a screen, a projector, a multi-media device, a monitor, TV screen, LCD screen, an electronic device, a plasma screen, etc.

Further, a first frequency is determined based on a speech sample of the person. A second frequency corresponding to the brain of the person is determined based on the first frequency. The second frequency is further divided into fifty sub-frequencies based on a mathematical formula computed by the processor 102 of FIG. 1. The fifty sub-frequencies are mapped against the fifty arcs of the brain to locate the exact spot of the energy blockage in form of arc number in the brain. A block-breaking frequency associated with the arc representing the energy blockage is determined from the fifty sub-frequencies.

The octave chart, as previously shown in Table 1, is used to calculate the first frequency, the second frequency, the fifty sub-frequencies and the block-breaking frequency. First, second, third and fourth octaves in the octave chart are used to calculate the frequencies. Further, a set of wave-patterns corresponding to the block-breaking frequency is determined. The set of wave-patterns comprises, but not limited to, sawtooth waveform, triangular waveform, square waveform, sine waveform, etc. Sound signals, based on the set of wave-patterns, are heard by the person 107 thereby healing the blocked energy area of the brain. The sound signals have a frequency range from 20 Hz to 20,000 Hz and are audible by the person. The sound signals are heard by the person at recurrent intervals in a time frame to monitor condition of the person.

Figure 4:
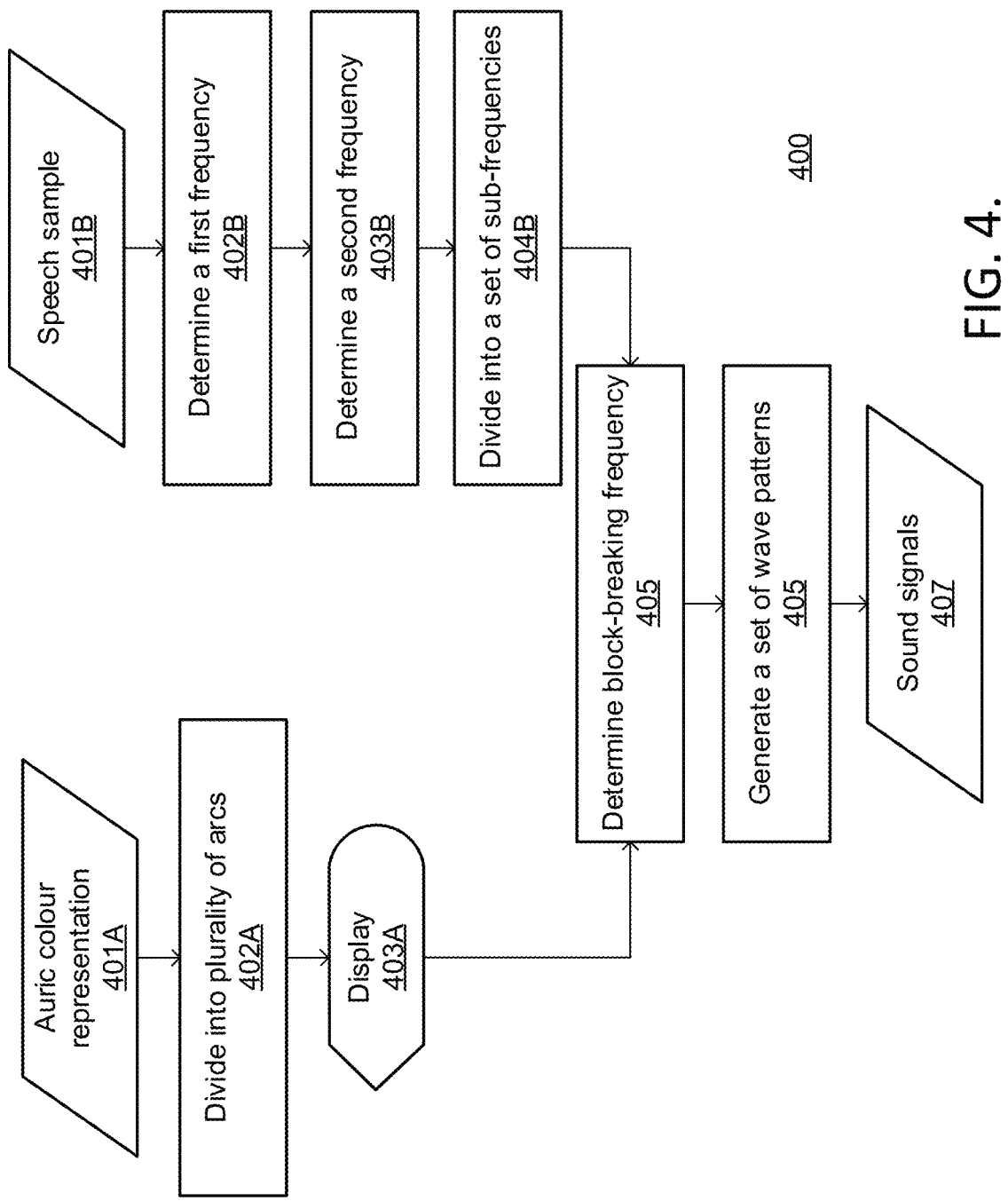
FIG. 4 shows a method for producing sound signals according to another embodiment of the invention.

FIG. 4 shows a method 400 of the invention for producing sound signals. At step 401A, an auric color representation of a body part of the person is captured. The auric color representation represents one or more blocked energy areas in the body part of the person. The body part may include but is not limited to brain, respiratory system, digestive system, circulatory system, excretory system, nervous system, etc. The energy areas comprise blocked energy areas, unblocked energy areas, or a combinations of blocked energy areas and unblocked energy areas.

The auric color representation comprises different colors associated with different amount of energies in the body part. The colors in the auric color representation change according to state of the body part. Energies of the body part are associated to colors, chakras and musical tones as they all resonate to same frequency. In other words, sound, light and color are interconnected at source. Thus, different colors in the auric color representation demonstrate different energy levels of the captured body part.

At step 402A of the FIG. 4, the auric color representation is divided into a plurality of arcs by a processor 102 (previously shown in the FIG. 1). The processor 102 may be, but not limited to, a microprocessor, a microcontroller, a graphical processor, a GPU, graphic cards, a GPGPU, etc. The plurality of arcs represents a plurality of images of the body part. Number of arcs may depend upon various parameters, such as, the body part to be treated, amount of energy blockage in the body part, to what extent the energy blockage is to be treated, etc. In an embodiment of the invention, the plurality of arcs is fifty, where each arc corresponds to 7.2 degrees. At step 403A, the plurality of arcs is displayed.

In addition, at step 401B, a speech sample of the person is taken by using, but not limited to, a microphone, a voice recorder, a multimedia device, etc. A speech frequency is determined based on the speech sample. The speech frequency is as unique to every human body, as is the fingerprint. In general, the speech frequency of the person lies between second and third octaves in the octave chart.

At step 402B, a first frequency is determined on basis of the speech frequency of the person. The first frequency is determined by comparing the speech frequency to a nearest value in the octave chart (shown in Table 1). The speech frequency is associated with the fifth energy center or chakra. In other words, the speech frequency corresponds to throat signals, where the throat area forms the fifth energy center or fifth chakra among the seven chakras. The first frequency thus obtained is associated with the fifth energy center or fifth chakra among the seven chakras.

At step 403B, a second frequency corresponding to the body part of the person is determined based on the first frequency. Exact location of the first frequency is determined in the octave chart to calculate frequency values of all other six energy centers or chakras from the octave chart. Four values down and two values up the first frequency in the octave chart leads to determination of frequency values of the six energy centers or chakras. Frequency value of the energy center associated with the body part having blocked energy areas to be treated is the second frequency value. Thus, the second frequency value corresponds to the body part to be treated.

At step 404B, the second frequency is divided into a set of sub-frequencies based on a mathematical formula computed by the processor 102 (shown in the FIG. 1). The set of sub-frequencies may range from two to fifty. The set of sub-frequencies is associated with the energy center or chakra of the body part of the person. Different body parts lead to different set of sub-frequencies. Moreover, the set of sub-frequencies is associated with the plurality of arcs obtained at the step 402A. As many as arcs in the plurality of arcs, as many as sub-frequencies in the set of sub-frequencies are generated. Thus, there is one-to-one correlation between the plurality of arcs and the set of sub-frequencies. In an embodiment of the invention, the set of sub-frequencies is fifty.

At step 405, a block-breaking frequency is determined based on correlation of the set of sub-frequencies obtained at the step 404B with the displayed plurality of arcs at step 403A. The block-breaking frequency corresponds to frequency of the blocked energy area of the body part. In an embodiment of the invention, the fifty sub-frequencies are correlated with the fifty arcs to determine a block-breaking frequency among the fifty sub-frequencies for an arc representing energy blockage. Each arc in the plurality of arcs is associated with each block-breaking frequency in the set of sub-frequencies.

At step 406, a set of wave-patterns corresponding to the block-breaking frequency is determined. The set of wave-patterns comprises, but not limited to, sawtooth waveform, triangular waveform, square waveform, sine waveform, etc. At step 407, sound signals are produced based on set of wave-patterns. The sound signals are heard by the person thereby healing the blocked energy area of the body part. The sound signals have a frequency range from 20 Hz to 20,000 Hz and are audible by the person. The sound signals are heard by the person at recurrent intervals in a time frame to monitor condition of the person. According to an embodiment of the invention, the sound signals are heard by the person 107 for the time frame as recommended by a psychiatrist.

According to another embodiment of the invention, the sound signals are heard by the person for a period of, but not limited to, 3 minutes-30 minutes. At the end of the period, the process flow jumps back to the step 401A, where the auric color representation is captured again, divided into a plurality of arcs at step 402A and displayed at the step 403A. If the display shows that the energy areas of the body part of the person are still blocked, the process flow jumps to the step 407, where the sound signals are again heard by the person for a period of, but not limited to, 30 minutes. This process is repeated until the auric color representation of the body part of the person shows healed energy areas with minimum or zero blockage. According to another embodiment of the invention, the sound signals are heard by the person 107 for the period as recommended by a psychiatrist.

According to another embodiment of the invention, different wave-patterns in the set of wave-patterns obtained at the step 406 are randomly heard by the person for a time period. Thus, the set of wave-patterns may comprise any waveform for any time duration.

According to another embodiment of the invention, different wave-patterns in the set of wave-patterns obtained at the step 406 are heard by the person for a period of 27 minutes in a particular sequence. For instance, the square waveform is heard for first 6 minutes followed by the saw tooth waveform for 4 minutes, then the triangular waveform for next 8 minutes and then sine waveform for last 9 minutes respectively. The square waveform and the saw tooth waveform are believed to break the energy blockage in the body part of the person, whereas the triangular waveform and the sine waveform are believed to smooth the energy blockage in the body part of the person.

Figure 5:
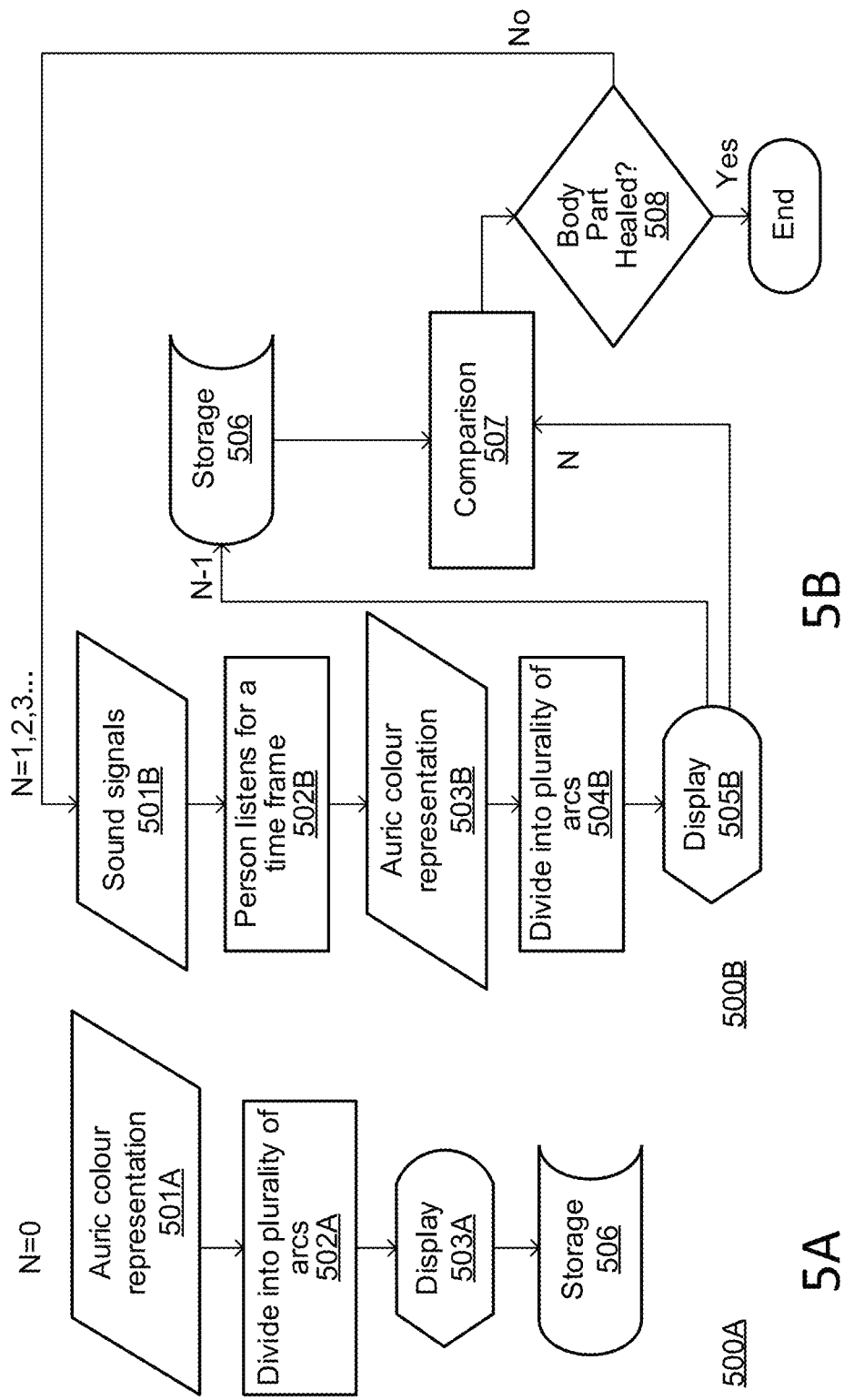
FIG. 5A-5B shows a process flow representation of monitoring energy blocked areas in a person according to another embodiment of the invention.

FIG. 5A-5B shows a process flow representation 500A-500B of monitoring energy blocked areas in a person. Sound based healing to heal the energy blocked areas at various body parts in the person comprises of generating sound signals of a certain frequency, which when heard by the person leads to healing of the blocked energy areas in the body parts. The body parts may include, but not limited to, brain, respiratory system, digestive system, circulatory system, excretory system, nervous system, etc. Moreover, each body part of the person is associated with a particular frequency. The sound-based healing involves generating sound signals of the particular frequency. By using sound based healing, affected body part is healed inside out.

FIG. 5A shows a process flow 500A for display and storage of auric color representation at an initial stage of a plurality of stages. The plurality of stages is referred to as "N", where N=0 represents the initial stage, N=1 represents first stage, N=2 represents second stage and so on. According to the FIG. 5A, an auric color representation of the body part of the person is captured initially at step 501A. The auric color representation represents one or more energy areas in the body part of the person. The energy areas comprise blocked energy areas, unblocked energy areas, or a combination of blocked energy areas and unblocked energy areas. The auric color representation comprises different colors associated with different amount of energies in the body part. Thus, different colors in the auric color representation demonstrate different energy levels of the captured body part.

At step 502A, the auric color representation obtained at the step 501A is divided into a plurality of arcs by the processor 102 (previously shown in the FIG. 1). The plurality of arcs represents a plurality of images of the body part. In an embodiment of the invention, the plurality of arcs is fifty, where each arc corresponds to 7.2 degrees.

At step 503A, the plurality of arcs is displayed on a display device 103, previously shown in FIG. 1. The display device 103 is, but not limited to, a screen, a projector, a multi-media device, a monitor, TV screen, LCD screen, an electronic device, a plasma screen, etc. Further, the plurality of arcs is stored in a storage at step 506. The storage includes, but not limited to, high-speed random-access memory, non-volatile memory, magnetic disk storage device, optical storage device, flash memory (e.g., NAND, NOR), hard drives, soft drives etc.

Further, FIG. 5B represents a process flow 500B for monitoring healing of body parts. The process flow 500B represents the plurality of stages, N=1, 2, 3, . . . , and so on. At step 501B of the FIG. 5B, sound signals of the frequency corresponding to the body part to be healed are generated by the audio device 106 (previously shown in FIG. 1). The audio device 106 produces sound signals, based on the set of wave-patterns, to be heard by the person thereby healing the blocked energy area of the body part. The sound signals have a frequency range from 20 Hz to 20 MHz and are audible by the person.

At step 502B, the sound signals are heard by the person for a specific time frame. At the end of the time frame, at step 503B, an auric color representation of the body part of the person is captured. The auric color representation obtained at the step 503B represents energy areas in the body part of the person after the person has heard the sound signals for the specific time frame.

At step 504B, the auric color representation obtained at the step 503B is divided into a plurality of arcs by the processor 102 (previously shown in the FIG. 1). The plurality of arcs represents a plurality of images of the blocked energy areas in the body part after the person has heard the sound signals for the specific time frame. Number of arcs may depend upon various parameters, such as, the body part to be treated, amount of energy blockage in the body part, to what extent the energy blockage is to be treated, etc. In an embodiment of the invention, the plurality of arcs is fifty, where each arc corresponds to 7.2 degrees.

Further, at step 505B, the plurality of arcs obtained at the step 504B are displayed on a display device. The display device of the step 505B may be same or different from the display device 103 of the step 503A. The display device includes, but not limited to, a screen, a projector, a multi-media device, a monitor, TV screen, LCD screen, an electronic device, a plasma screen, etc. In addition, the plurality of arcs obtained and displayed at the steps 504B and 505B respectively, are stored in the storage at step 506. The storage includes, but not limited to, high-speed random-access memory, non-volatile memory, magnetic disk storage device, optical storage device, flash memory (e.g., NAND, NOR), hard drives, soft drives etc.

Moreover, at step 507, the display obtained at the step 505B is compared to previously stored display from previous stage (N−1) to determine healed energy areas in the treated body part. For instance, at stage, N=1, the display obtained at the step 505B is stored in the storage at the step 506 and is compared to the display stored in the storage from stage N=0. Similarly, at stage N=2, the display obtained at the step 505B is stored in the storage at the step 506 and is compared to the display stored in the storage from previous stage N=1, and so on.

Based on result of the comparison at step 507, it is determined at step 508, if the body part under treatment is healed or not. If the body part is not healed, the process flow 500B jumps back to the step 501B, otherwise the process flow 500B is ended. The process flow is repeated until the body part is healed or as directed by physician.

Further, according to an embodiment of the invention, the person is tested using Internationally Approved Scales, such as, but not limited to, HAM-A, HAM-D, PHQ, etc. to assess and quantify nature and severity of dysfunctionality of the person. These scales are refilled in consultation with the person after completion of the process. The difference between first score of the scales and scores at the end of the therapy are compared to evaluate improvement of the person.

Figure 6:
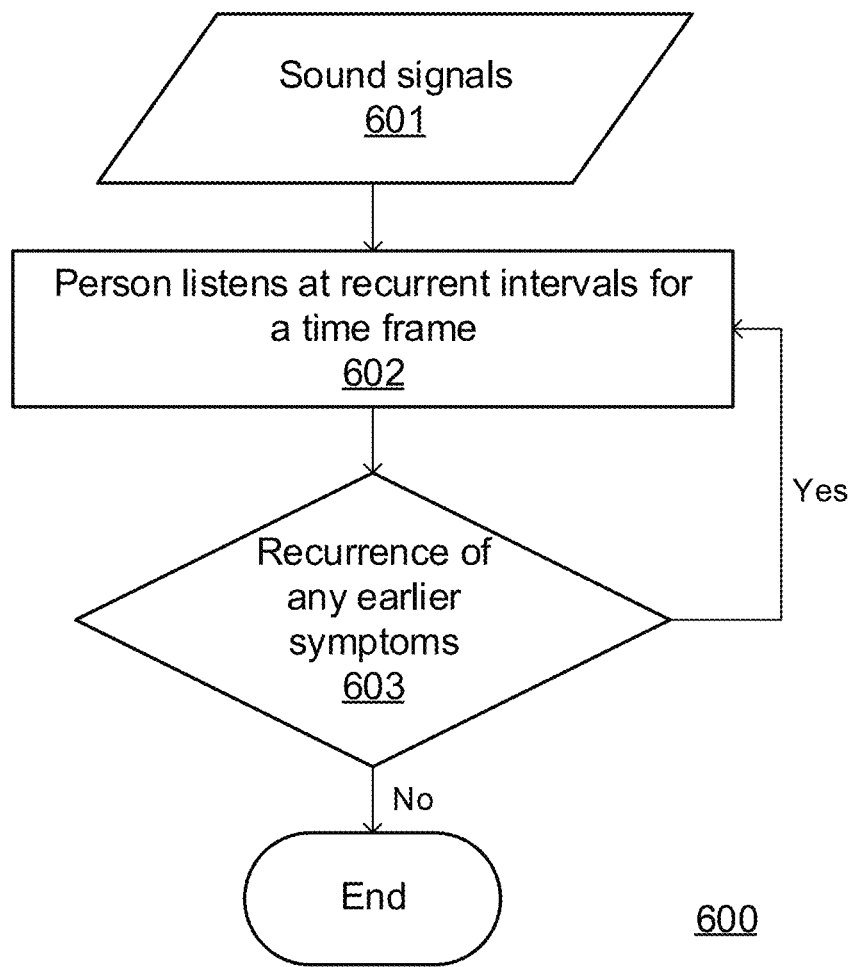
FIG. 6 represents a process flow to continuously monitor health of a person according to another embodiment of the invention.

According to another embodiment of the invention, FIG. 6 represents a process flow 600 to continuously monitor health of a person. Sound based healing to heal the energy blocked areas at various body parts in the person comprises of generating sound signals of a certain frequency, which when heard by the person leads to healing of the blocked energy areas in the body parts. The body parts may include, but not limited to, brain, respiratory system, digestive system, circulatory system, excretory system, nervous system, etc. Moreover, each body part of the person is associated with a particular frequency. The sound based healing involves generating sound signals of the particular frequency.

At step 601 of the FIG. 6, sound signals of the frequency corresponding to the body part are generated by the audio device 106, as previously shown in FIG. 1. The audio device 106 produces sound signals, based on the set of wave-patterns, to be heard by the person thereby healing the blocked energy area of the body part. The sound signals have a frequency range from 20 Hz to 20,000 Hz and are audible by the person.

At step 602, the sound signals are heard by the person at recurrent intervals for a specific time frame. According to another embodiment of the invention, the sound signals are heard by the person for an interval of, but not limited to, 3 minutes-30 minutes. Further, the person listens to the sound signals 25-30 times, based on extent of energy blockage in the body part of the person. The person may further listen to the sound signals in one or more sittings as prescribed by a psychiatrist. Further, the psychiatrist may be, but not limited to, a medical practitioner, a health practitioner, a psychologist, a counsellor, a therapist, a psychoanalyst, a psychotherapist, a shrink, a doctor, a healer. an alienist, an analyst, etc.

At step 603 of the FIG. 6, the person is continuously monitored for recurrence of any earlier symptoms. The symptoms may vary depending upon extent of the energy blockage in the body part. The symptoms may include, but not limited to, mental and physical disorders, depression, panic, bipolar, post-traumatic stress disorder, agoraphobia, OCD (obsessive compulsive disorder), chemical dependency, perceptual condition, memory issues, ADD (attention deficit disorder—Hyperactivity), PDD (Pervasive Developmental Disorder), Cognitive Issues, Stress, anxieties, fear, instability, emotional imbalance, low energy, fatigue, scarcity of creativity, dearth of imagination, etc. Moreover, the symptoms may vary from a person to person.

At the step 603, if it is determined that the person is showing any earlier symptoms, the process flows jump back to the step 602, otherwise the process flow is ended.

The present invention is described by the following examples which is one of several embodiments.

EXAMPLES

It is clinically known that various physical and mental illnesses show changes in the brain. The inventors have used symptoms of stress, anxiety, and depression as the main presenting symptoms of the 20 subjects that were studied. TMS is used for the comparison purposes for the effectiveness of the invention as TMS is an already established treatment for various medical conditions particularly anxiety and depression and approved by Federal Drug Administration (FDA).

The inventors have produced the sound signals for the subjects based on the system and method of the invention. 10 subjects Ten (10) subjects are given treatment with the sound signals from the method of the invention called as TSS (Transcranial Sound Stimulation) group and remaining 10 were treated with TMS (Transcranial Magnetic Stimulation) called as TMS group. The results of both are presented herewith.

In all the 20 subjects, diagnoses and their severity are established by using clinical scales HAM-A, HAM-D and Aura photography. HAM-A and HAM-D scales are well established diagnostic clinical scales in the medical field for years. In addition, aura photography is used as a diagnostic tool to assess percentage of energy blocks in the brain due to stress anxiety and depression.

TMS Group treatment: A total of 20-36 TMS treatments are externally used at the left frontal area of the brain. The duration of each treatment is 17-30 minutes/treatment over a total duration of 3-9 weeks.

TSS group treatment: Sound frequency is calculated using the voice pitch analysis to measure the voice frequency first for the individual subjects in the TSS group. Then, the individual voice frequency is used to calculate the brain frequency by using Nirvana Sage Sound Frequency Analyzer and particular frequency tone is generated by Tone generator. The brain frequency is given in four wave forms called Square, Sawtooth, Triangle and Sine waves. The location and duration of treatments is calculated and adjusted as per clinical symptoms of the subjects studied. Commonly used electronic devices such as phone, lap-top and/or desktop are used for the sound delivery using ears between 45-85 percent volume for about 25-30 minutes per treatment, once or twice a day for a total of 3-9 weeks.

The scores on clinical scales for anxiety and depression (HAM-A and HAM-D scores respectively) along with aura pictures are taken before, during and after the treatments.

TMS group: The HAM-A scores for the subjects before the treatment are in range of 21-35 and HAM-D scores are in the range of 22-27.

The subjects in both the groups have a history of clinical anxiety and depression and it has been observed that the scores on the clinical scales and the energy blocks (red/pink color) significantly reduced and correlate positively with the clinical improvement. Thus, the subjects responded to the treatment provided. The below table 2-3 shows scores on clinical scales. All scores improve mild to moderately after treatments and the subject significantly improves from depression and moderately from anxiety. Thus, the present invention provides effective healing for the subjects.

TABLE 2

Scores of TMS group

| Clinical scales | Range before the treatment | Scores after the treatment | | |
| --- | --- | --- | --- | --- |
| | | Below 5 | 5-9 | 10 & Above |
| HAM-A Score | 21-35 | 2 | 6 | 2 |
| HAM-D Score | 22-27 | 2 | 7 | 1 |

TABLE 3

Scores of TSS Group

| Dates of clinical scales | Range | Below 5 | 5-9 | 10 & Above |
| --- | --- | --- | --- | --- |
| HAM-A Score | 18-32 | 2 | 6 | 2 |
| HAM-D Score | 8-31 | 5 | 4 | 1 |

Some portions of the description describe the embodiments of the invention in terms of algorithms and figurative representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, processes, or operations described herein may be performed or implemented with one or more hardware, software or firmware modules, alone or in combination with other devices. In one embodiment, a software module is implemented with a computer program product comprising a computer-readable medium containing computer program code, which can be executed by a computer processor for performing any or all of the steps, processes, or operations described.

Although the present invention has been described in terms of certain embodiments, various features of separate embodiments can be combined to form additional embodiments not expressly described. Moreover, other embodiments apparent to those of ordinary skill in the art after reading this disclosure are also within the scope of this invention. Furthermore, not all of the features, aspects and advantages are necessarily required to practice the present invention. Thus, while the above detailed description has shown, described, and pointed out novel features of the invention as applied to various embodiments, it will be understood that various omissions, substitutions, and changes in the form and details of the apparatus or process illustrated may be made by those of ordinary skill in the technology without departing from the spirit of the invention. The inventions may be embodied in other specific forms not explicitly described herein. The embodiments described above are to be considered in all respects as illustrative only and not restrictive in any manner. Thus, scope of the invention is indicated by the following claims rather than by the foregoing description.

The invention claimed is:

1. A system for producing sound signals, the system comprising:
    an image capturing device to capture an auric color representation of at least one body part of a person, wherein the auric color representation represents at least one blocked energy area of the at least one body part;
    at least one processing device configured to divide the auric color representation into a plurality of arcs;
    a display device to display the plurality of arcs processed by the at least one processing device;
    a transcranial sound stimulation device to determine at least one block-breaking frequency corresponding to the at least one blocked energy area of the least one body part of the person;
    a tone generator to generate a set of wave-patterns corresponding to the at least one block-breaking frequency; and
    an audio device to produce sound signals based on the set of wave-patterns.

2. The system according to claim 1, wherein the auric color representation represents energy areas of the at least one body part.

3. The system according to claim 2, wherein the energy areas comprise at least one of blocked energy areas, unblocked energy areas, or a combination thereof.

4. The system according to claim 1, wherein the plurality of arcs represent a plurality of images of the at least one body part.

5. The system according to claim 1, wherein the transcranial sound stimulation comprises a frequency determination module configured to determine the at least one block-breaking frequency corresponding to the at least one blocked energy area based on a correlation of a set of sub-frequencies with the plurality of arcs.

6. The system according to claim 5, wherein the frequency determination module is configured to:
    determine a first frequency based on a speech sample of the person;
    determine a second frequency corresponding to the at least one body part based on the first frequency;
    divide the second frequency into the set of sub-frequencies, and
    determine the at least one block-breaking frequency corresponding to the at least one blocked energy area based on the correlation of the set of sub-frequencies with the plurality of arcs.

7. The system according to claim 1, wherein the set of wave-patterns comprises at least one of sawtooth wave, triangular wave, square wave, sine wave, or a combination thereof.

8. The system according to claim 1, wherein the sound signals can be heard by the person to heal the at least one blocked energy area of the at least one body part.

9. The system according to claim 8, wherein the sound signals are to be heard by the person at recurrent intervals in a time frame to monitor a condition of the person.

10. A method for producing sound signals, the method comprising:
    capturing an auric color representation of at least one body part of a person by an image capturing device, wherein the auric color representation represents at least one blocked energy area of the at least one body part;
    dividing the auric color representation into a plurality of arcs by a processing device;
    displaying the plurality of arcs by a display device;
    determining at least one block-breaking frequency corresponding to the at least one blocked energy area by a transcranial sound stimulation device;
    generating a set of wave-patterns corresponding to the at least one block-breaking frequency by a tone generator; and
    producing sound signals based on the set of wave-patterns by an audio device.

11. The method according to claim 10, wherein the auric color representation represents energy areas of the at least one body part.

12. The method according to claim 11, wherein the energy areas comprise at least one of blocked energy areas, unblocked energy areas, or a combination thereof.

13. The method according to claim 10, wherein the plurality of arcs represents a plurality of images of the at least one body part.

14. The method according to claim 10, wherein the transcranial sound stimulation comprises a frequency determination module configured to determine the at least one block-breaking frequency corresponding to the at least one blocked energy area based on a correlation of a set of sub-frequencies with the plurality of arcs.

15. The method according to claim 14, wherein the frequency determination module is configured to:
    determine a first frequency based on a speech sample of the person;
    determine a second frequency corresponding to the at least one body part based on the first frequency;
    divide the second frequency into the set of sub-frequencies, and
    determine the at least one block-breaking frequency corresponding to the at least one blocked energy area based on the correlation of the set of sub-frequencies with the plurality of arcs.

16. The method according to claim 10, wherein the set of wave-patterns comprises at least one of sawtooth wave, triangular wave, square wave, sine wave, or a combination thereof.

17. The method according to claim 10, wherein the sound signals can be heard by the person to heal the at least one blocked energy area of the at least one body part.

18. A non-transitory computer readable medium storing instructions thereon that, when executed using one or more processors, cause the one or more processors to execute operations comprising:

capturing an auric color representation of at least one body part of a person by an image capturing device, wherein the auric color representation represents at least one blocked energy area of the at least one body part;

dividing the auric color representation into a plurality of arcs by a processing device;

displaying the plurality of arcs by a display device;

determining at least one block-breaking frequency corresponding to the at least one blocked energy area by a transcranial sound stimulation device;

generating a set of wave-patterns corresponding to the at least one block-breaking frequency by a tone generator; and producing sound signals based on the set of wave-patterns by an audio device.

19. The non-transitory computer readable medium according to claim 18, wherein the auric color representation represents energy areas of the at least one body part.

20. The non-transitory computer readable medium according to claim 14, wherein the energy areas comprise at least one of blocked energy areas, unblocked energy areas, or a combination thereof.

\* \* \* \* \*